United States Patent [19]

Stapp

[11] 4,126,756

[45] Nov. 21, 1978

[54] ALKENOL PRODUCTION

[75] Inventor: Paul R. Stapp, Bartlesville, Okla.

[73] Assignee: Phillips Petroleum Company, Bartlesville, Okla.

[21] Appl. No.: 782,603

[22] Filed: Mar. 29, 1977

Related U.S. Application Data

[62] Division of Ser. No. 651,864, Jan. 23, 1976, Pat. No. 4,039,594, which is a division of Ser. No. 484,261, Jun. 28, 1974, Pat. No. 3,960,973.

[51] Int. Cl.$^2$ .................. C07C 29/00; C07C 33/05
[52] U.S. Cl. .................................. 568/879; 568/823
[58] Field of Search .......... 260/638 R, 617 R, 617 M; 568/879, 823

[56] References Cited

U.S. PATENT DOCUMENTS 3,706,809  12/1972  Moroe et al. ............... 260/665 R

FOREIGN PATENT DOCUMENTS 1,228,991  4/1971  United Kingdom ............... 260/638 R Primary Examiner—Joseph E. Evans

[57] ABSTRACT

The yield of alkenols and cycloalkenols is substantially improved by carrying out the reaction of olefins with formaldehyde in the presence of selected catalysts. In accordance with one embodiment, alk-3-en-1-ols are produced in good yields from isobutylene and formaldehyde in the presence of organic carboxylic acid salts of Group IB metals.

7 Claims, No Drawings

ALKENOL PRODUCTION

This application is a division of my copending Ser. No. 651,864, filed Jan. 23, 1976, now U.S. Pat. No. 4,039,594, issued Aug. 2, 1977, which in turn was a division of my Ser. No. 484,261, filed June 28, 1974, now U.S. Pat. No. 3,960,973, issued June 1, 1976.

This invention relates to an improved process for the production of alkenols. In accordance with another aspect, this invention relates to an improved process for producing increased yields of alkenols by the reaction of olefins with formaldehyde in the presence of selected catalysts. In accordance with another aspect, alkenols are produced from olefins and formaldehyde in the presence of catalysts comprising carbonyls or oxides of Group VIB metals. In accordance with another aspect, this invention relates to an improved process for the production of increased yields of alkenols from formaldehyde and olefins in the presence of catalysts comprising organic carboxylic acid salts of Group IB metals. In accordance with a further aspect, this invention relates to the use of alkali metal or alkaline earth metal bisulfites as catalysts for improving the yield of alkenols from olefins and formaldehyde. In accordance with another aspect, this invention relates to the use of compounds of metals of Groups VB, VIIB, and VIII for increasing the yield of alkenols from olefins and formaldehyde. In accordance with a further aspect, this invention relates to the use of fluorided alumina as a catalyst for the conversion of olefins and formaldehyde to alkenols.

Accordingly, an object of this invention is to provide an improved process for production of alkenols.

Another object of this invention is to provide novel catalysts for increasing the yield of alkenols.

A further object of this invention is to provide an economically feasible process for the production of alkenols whereby high yields of desired products are obtained.

Other objects and aspects, as well as the several advantages of the invention, will be apparent to those skilled in the art upon reading the specification and the appended claims.

In accordance with the invention, it has been found that alkenols are obtained in high yields and high purity by reacting an olefin with formaldehyde in the presence of a catalyst selected from the group consisting of (1) carbonyls and oxides of metals chosen from Group VIB, (2) organic carboxylic acid salts of the metals of Group IB, (3) alkali metal and alkaline earth metal bisulfites, (4) compounds of the metals of Groups VB, VIIB, and VIII, and (5) fluorided alumina.

In accordance with one specific embodiment, it has been found that alk-3-en-1-ols are obtained in high yields and high purity by reacting an olefin such as isobutylene with formaldehyde under liquid phase conditions in the presence of at least one of the above defined selected catalysts.

In accordance with a further embodiment of the invention, 3-methyl-3-buten-1-ol in high yields and high purity can be obtained by reacting isobutylene with formaldehyde in the presence of one or more of the above defined selected catalysts.

Catalysts suitable for use in the instant invention are selected from one of the following groups:

A. A suitable catalyst can be selected from the carbonyls or the oxides of metals from Group VIB of the Periodic Table, i.e., chromium, molybdenum, and tungsten. If a metal carbonyl is employed, it is preferred though not necessary that a trihydrocarbyl phosphine or trihydrocarbyl phosphite be employed as a catalyst modifier. The amount of said modifier employed is generally from 1 to 6, inclusive, mols of modifier per mole of metal carbonyl. If a metal oxide is employed, the catalyst may be, if desired, dispersed on a known support material such as silica, pumice, charcoal, kieselguhr, and the like. Specific examples of suitable catalysts include $MoO_2$, $WO_3$, $WO_3$ on silica, $Cr(CO)_6$, $Mo(CO)_6$ modified with triphenyl phosphine, $Mo(CO)_6$, and $W(CO)_6$.

B. Suitable catalysts can also be selected from the organic carboxylic acid salts of the metals of Group IB of the Periodic Table, i.e., copper, silver, and gold. These organic carboxylic acid salts can be represented by the general formula $(R-CO_2-)_nM$ wherein R is hydrogen or a hydrocarbyl radical having from 1–19 carbon atoms and wherein $n$ is an integer which is equal to the valence of the metal M in the salt, and wherein M is one of copper, silver, or gold. Specific examples of suitable catalysts from this group include silver acetate and cupric acetate.

C. Other suitable catalysts can be selected from the alkali or alkaline earth metal bisulfites. These salts can be represented by the following general formula, $M'(HSO_3)_z$, wherein M' is an alkali or alkaline earth metal such as sodium or calcium and $z$ represents the valence of said metal in the salt. Specific examples of suitable bisulfites include sodium bisulfite and calcium bisulfite.

D. Another group of suitable catalysts consists of compounds of the metals of Groups VB, VIIB, and VIII of the Periodic Table, e.g., vanadium, manganese, palladium, iron, and rhodium. These compounds can be represented by the general formula $[M''(Z)_q]_x$ wherein M'' is one of the metals from the above named Groups and wherein Z is an anion or neutral ligand which can be a single atom or group of atoms and wherein $q$ is an integer which when multiplied by the negative charge on Z as the anion equals the valence of M'' and wherein $x$ is an integer indicating that such compounds may be polymeric; however, $x$ will usually be 1 or perhaps 2. Specific examples of suitable catalysts from this group include rhodium trichloride, palladous cyanide, manganese (II) acetylacetonate, vanadium (III) acetylacetonate, vanadyl acetylacetonate, dicyclopentadienyl iron (ferrocene), and $\mu,\mu'$-dichlorotetranitrosyldiiron, $[Fe(NO)_2Cl]_2$.

E. Another group of suitable catalysts are the fluorided aluminas containing from about 5 to about 30 weight percent fluorine. These catalysts can be prepared by methods well known in the art such as treatment of alumina with anhydrous HF or impregnation of alumina with aqueous HF or ammonium fluoride.

Olefins which are suitable for use in the instant invention are those having at least one allylic hydrogen, i.e., having the basic structure

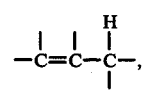

and from 3 to 20 carbon atoms per molecule. The olefinic double bond in said compounds can be a part of a carbocyclic ring. Furthermore, substituents which are essentially inert under the reaction conditions can also be present in the olefinic reactant. Typical examples of such substituents include —CN, —Cl, —OCH$_3$, —CO$_2$CH$_2$CH$_3$, and the like. However, one skilled in the art would not employ the metal carbonyl catalysts described in "A" above with olefins having a —CN substituent since such would be expected to consume or inactivate the catalyst. Of the olefinic reactants broadly suitable, the presently preferred olefinic compounds are those containing only carbon and hydrogen such as the alkenes or cycloalkenes. Examples of suitable olefinic reactants include propylene, isobutylene, α-methylstyrene, 1-methyl-4-isopropenylcyclohexene, 1-methylcyclohexene, methallyl chloride, methyl isopropenyl ether, 5-methyl-5-hexenenitrile, and the like, and mixtures thereof.

Formaldehyde is employed as the aldehyde reactant in the instant invention. However, the formaldehyde reactant may be employed in any of its well-known, commercially available, nonaqueous forms such as the cyclic trimer, 1,3,5-trioxane, or the polymeric form, paraformaldehyde.

In carrying out the invention, the temperature can be broadly from 150° C.-250° C. The time employed for the reaction of the instant invention can be from about three minutes up to 24 hours and preferably from 15 minutes to two hours. The reaction of the instant invention is generally carried out under autogeneous pressure, but, if desired, pressure from an inert gas such as nitrogen or helium can also be applied up to about 1,000 psig of the inert gas. However, no significant advantages are expected from the use of the inert gas pressure in this invention.

The amount of catalyst, selected from the above-described suitable groups of catalysts, which is employed in the reaction of this invention is generally from 0.1 to 10, preferably from 0.2 to 5, percent by weight, based on the weight of the formaldehyde charged to the reaction mixture.

The molar ratio of olefinic reactant to formaldehyde for the reaction of the instant invention is broadly from 1/1 up to 20/1, preferably from 5/1 up to 13/1. However, if the olefinic reactant is especially expensive, it is within the scope of this invention to employ a molar excess of the formaldehyde to promote complete conversion of the olefinic reactant. In such instances, up to about 20 mols of formaldehyde per mol of olefinic reactant can be employed.

It is preferred to carry out the reaction of the instant invention in the presence of an essentially inert added diluent. However, the use of an added diluent is not necessary to the practice of the instant invention. It is also within the scope of the instant invention to employ the reaction product, e.g., an alkenol, as the diluent for further reaction of the olefinic reactant and formaldehyde according to the instant invention. If a diluent is employed, the amount used will generally be in the range of from 10 to 1,000 parts by weight of diluent per one part by weight of formaldehyde in the reaction mixture. Examples of suitable diluents which can be added include benzene, cyclohexane, heptane, chlorobenzene, diphenyl ether, sulfolane, 3-methylsulfolane, and the like, and mixtures thereof.

When employing catalysts which are soluble in the reaction mixture, the final reaction mixture can be distilled directly to yield unconsumed reactants which can be recycled to the reaction zone, product(s), and residue which generally contains the catalyst which can also be recycled to the reaction zone. When employing a catalyst which is insoluble or only partially soluble in the reaction mixture, the catalyst is usually removed by filtration, then the filtrate distilled to recover unconsumed reactants and product(s).

The alkenols which are the principal products of the reaction according to the instant invention have utility in several areas of the chemical arts. They may be employed as blending agents for motor fuels or as solvents for lacquers, perfumes, and the like. They can be converted to halides or ethers, or nitrated for the production of diesel fuel ignition promotors. They may also be halogenated, oxidized, hydrogenated, dehydrogenated, or dehydrated, the latter operation producing conjugated diolefins which have important well-known uses in the art. A small amount of conjugated diolefin may sometimes be found in the products of the reaction, according to the instant invention. Presumably, a small amount of the alkenol can be dehydrated in situ to provide the diolefin in the product.

EXAMPLE I (Control Run)

A one-liter stainless steel autoclave equipped with stirring means was charged with 200 ml (176 g) of benzene, 16 g of 94.4% paraformaldehyde (0.503 mol), and 278 g (4.964 mol) of isobutylene. The mixture was then heated at 200° C. for one hour while the pressure (autogeneous) ranged from 1,150 down to 1,050 psig. The reactor was cooled and vented, and the contents filtered. The filtrate was fractionally distilled to provide four fractions which were analyzed by gas-liquid chromatography (GLC) procedures. The analysis revealed a total of 13.18 g (0.153 mol) of 3-methyl-3-buten-1-ol in the four fractions which is a 30% yield based on the formaldehyde starting material. A small amount (about 0.4 g) of the formate ester of the above alkenol was also detected in the distilled product. A considerable amount of unreacted formaldehyde was detected in the reaction mixture, but it was not measured.

EXAMPLE II (Invention)

A one-liter autoclave was charged with 200 ml (176 g) of benzene, 16 g of 94.4% paraformaldehyde (0.503 mol), 0.5 g fluorided alumina (having about 25 weight percent fluorine), and 295 g (5.26 mol) of isobutylene. The reaction mixture was heated at 200° C. for one hour while the pressure (autogeneous) ranged from 1,700 down to 1,450 psig. The reactor was cooled, vented, and the contents filtered. The filtrate was fractionally distilled into three fractions. Analysis of the fractions by GLC indicated that 25.38 g (0.295 mol) of 3-methyl-3-buten-1-ol had been obtained for a yield of 59% based on the starting formaldehyde. A small amount (0.85 g) of the formate ester of the alkenol was detected in the distilled product, and considerable unreacted formaldehyde was noticed in the product mixture but was not measured.

EXAMPLE III (Invention)

A one-liter stainless steel autoclave was charged with 200 ml (176 g) benzene, 16 g of 94.4% paraformaldehyde (0.503 mol), 0.5 g of sodium bisulfite, and 312 g (5.57 mol) of isobutylene. The mixture was heated at 200° C. for one hour while the pressure (autogeneous) ranged from 1,900 down to 1,550 psig. The reactor was cooled, vented, and the contents filtered. The filtrate was fractionally distilled into four fractions. Analysis of the fractions by GLC indicated that 27.18 g (0.316 mol) of 3-methyl-3-buten-1-ol had been obtained for a yield of 63% based on the starting formaldehyde. GLC analysis also indicated the presence of 0.80 g of the formate ester of the alkenol in the distilled product, and some unreacted formaldehyde was also detected in the reaction mixture but the quantity was not measured.

EXAMPLE IV (Invention)

A one-liter stainless steel autoclave was charged with 200 ml (176 g) of benzene, 16 g of 94.4% paraformaldehyde (0.503 mol), 1.0 g of silver acetate, and 320 g (5.714 mol) of isobutylene. The reaction mixture was heated at 200° C. for one hour while the pressure ranged from 2,250 to 1,925 psig. The reactor was cooled, vented, and the contents filtered. The filtrate was fractionally distilled into four fractions. Analysis of the fractions by GLC showed that 28.80 g (0.335 mol) of 3-methyl-3-buten-1-ol had been obtained for a yield of 67 percent based on the starting formaldehyde. GLC analysis also indicated the presence of 1.09 g of the formate ester of the alkenol in the distilled product.

EXAMPLE V (Control)

A one-liter stainless steel autoclave was charged with 200 ml (176 g) of benzene, 16 g of 94.4% paraformaldehyde (0.503 mol), 1.0 g of silver sulfate, and 315 g (5.625 mol) of isobutylene. The reaction mixture was heated for one hour at 200° C. while the pressure (autogeneous) ranged from 2,050 down to 1,750 psig. The reactor was cooled, vented, and the contents filtered. The filtrate was distilled into three fractions. Although no unreacted formaldehyde was detected, there was no evidence that 3-methyl-3-buten-1-ol had been produced in a recoverable amount. Also, a considerable amount of water had been formed in the reaction mixture. The product was not analyzed further.

EXAMPLE VI (Control)

Another run employing silver sulfate as catalyst was carried out but at a lower temperature. In this run a one-liter stainless steel autoclave was charged with 200 ml (176 g) of benzene, 16 g of 94.4% paraformaldehyde (0.503 mol), 1 gram of silver sulfate, and 305 g (5.446 mol) of isobutylene. The reaction mixture was heated at 150° C. for one hour with an autogeneous pressure of 325 psig. The reactor was cooled, vented, and the contents filtered. The filtrate was analyzed by GLC which indicated a yield of about 3% of 3-methyl-3-buten-1-ol based on the starting formaldehyde. A large amount of unreacted formaldehyde was also present, but the quantity was not measured.

EXAMPLE VII (Invention)

A one-liter stainless steel autoclave was charged with 200 ml (176 g) benzene, 16 g of 94.4% paraformaldehyde (0.503 mol), 1.0 g of cupric acetate monohydrate, and 385 g (5.446 mol) isobutylene. The reaction mixture was heated at 175°-200° C. for one hour while the pressure (autogeneous) ranged from 1,500-1,250 psig. The reactor was cooled, vented, and the contents filtered. Some metallic copper was removed during the filtration step. The filtrate was fractionally distilled into four fractions. Analysis of the fractions by GLC showed that 21.96 g (0.255 mol) of 3-methyl-3-buten-1-ol had been obtained for a yield of 51% based on the starting formaldehyde. GLC analysis also indicated that 0.84 g of the formate ester of the alkenol had been produced. A considerable amount of unreacted formaldehyde was detected in the product, but the quantity was not measured.

EXAMPLE VII (Invention)

A one-liter stainless steel autoclave was charged with 200 ml (176 g) of benzene, 16 g of 94.4% paraformaldehyde (0.503 mol), 0.5 g of chromium hexacarbonyl, $Cr(CO)_6$, and 325 g (5.804 mol) of isobutylene. The reaction mixture was heated at 200° C. for one hour. The reactor was cooled and vented, and the reaction mixture distilled into four fractions. GLC analysis of the fractions indicated that 26.16 g (0.304 mol) of 3-methyl-3-buten-1-ol had been obtained for a yield of 60% based on the starting formaldehyde. GLC analysis also indicated the presence of 1.38 g of the formate ester of the alkenol in the reaction mixture. Considerable unreacted formaldehyde was also noted in the reaction mixture, but the quantity was not measured.

EXAMPLE IX (Invention)

A one-liter stainless steel autoclave was charged with 200 ml (176 g) of benzene, 16 g of 94.4% paraformaldehyde (0.503 mol), 0.5 g of tungsten hexacarbonyl, $W(CO)_6$, and 275 g (4.911 mol) of isobutylene. The reaction mixture was heated at 200° C. for one hour. The reaction mixture was distilled into four fractions. GLC analysis of the fraction showed that 19.81 g (0.230 mol) of 3-methyl-3-buten-1-ol had been obtained for a yield of 46% based on the starting formaldehyde. The formate ester of the alkenol was also present (0.88 g) as indicated by GLC analysis. Considerable unreacted formaldehyde was also noted in the reaction mixture, but the quantity was not measured.

EXAMPLE X (Invention)

A one-liter stainless steel autoclave was charged with 250 ml (220 g) of benzene, 16 g of 95.4% paraformaldehyde (0.509 mol), 0.5 g molybdenum hexacarbonyl, $Mo(CO)_6$, and 300 g (5.357 mol) of isobutylene. The reaction mixture was heated at 200° C. for one hour while the pressure (autogeneous) ranged from 2,000 down to 1,350 psig. The reactor was cooled and vented, and the contents distilled into four fractions. GLC analysis of the fractions showed that 17.99 g (0.209 mol) of 3-methyl-3-buten-1-ol had been obtained for a yield of 41% based on the starting formaldehyde. The GLC analysis also indicated that 0.81 g of the formate ester of the alkenol had been obtained.

EXAMPLE XI (Invention)

A one-liter stainless steel autoclave was charged with 250 ml (220 g) of benzene, 16 g of 92.8% paraformaldehyde (0.495 mol), 0.5 g molybdenum hexacarbonyl, $Mo(CO)_6$, and 335 g (5.982 mol) of isobutylene. The reaction mixture was heated at 200° C. for two hours. The reactor was cooled, vented, and the contents filtered. A small amount of the filtrate was lost due to a spill. The filtrate was distilled into four fractions. GLC analysis of the fractions showed that 24.11 g (0.280 mol) of 3-methyl-3-buten-1-ol had been obtained for a yield of 57% based on the starting formaldehyde. The GLC analysis also indicated that 1.21 g of the formate ester of the alkenol had been obtained.

EXAMPLE XII (Invention)

A one-liter stainless steel autoclave was charged with 200 ml (176 g) of benzene, 16 g of 94.4% paraformaldehyde (0.503 mol), 0.5 g (1.9 mmol) of molybdenum hexacarbonyl, 0.5 g (1.9 mmol) of triphenylphosphine, and 295 g (5.268 mol) of isobutylene. The reaction mixture was heated at 200° C. for one hour. The reactor was cooled, vented, and the contents filtered. The filtrate was distilled into four fractions. GLC analysis of the fractions showed that 30.28 g (0.352 mol) of 3-methyl-3-buten-1-ol had been obtained for a yield of 70% based on the starting formaldehyde. GLC analysis also indicated that 0.97 g of the formate ester of the alkenol had also been obtained.

EXAMPLE XIII (Invention)

A one-liter autoclave was charged with 250 ml (220 g) of benzene, 31 g of 92.8% paraformaldehyde (0.959 mol), 1 gram of tungsten hexacarbonyl, $W(CO)_6$, and 280 g (5.00 mol) of 1-butene. The reaction mixture was heated at 225° C. for 6 hours while the pressure (autogeneous) ranged from 2,750 down to 2,300 psig. The reactor was cooled and vented and distilled into four fractions. GLC analysis of the fractions indicated that 16.56 g (0.192 mol) of 3-penten-1-ol (cis and trans) had been obtained for a yield of 20% based on the starting formaldehyde. However, GLC analysis also showed that 6.72 g of the formate ester of the alkenols had been obtained.

EXAMPLE XIV (Invention)

A one-liter stainless steel autoclave was charged with 200 ml (176 g) of benzene, 16 g of 94.4% paraformaldehyde (0.503 mol), 0.5 g of manganese (II) acetylacetonate, and 310 g (5.536 mol) of isobutylene. The reaction mixture was heated at 200° C. for one hour while the pressure (autogeneous) ranged from 2,000 down to 1,700 psig. The reactor was cooled, vented, and the contents filtered. The filtrate was distilled into four fractions. Analysis of the fractions by GLC showed that 24.92 g (0.290 mol) of 3-methyl-3-buten-1-ol had been obtained for a yield of 58% based on the starting formaldehyde. The analysis also showed that 0.88 g of the formate ester of the alkenol had been obtained.

EXAMPLE XV (Invention)

A one-liter stainless steel autoclave was charged with 200 ml (176 g) benzene, 16 g of 94.4% paraformaldehyde (0.503 mol), 0.5 g of ferrocene (dicyclopentadienyl iron), and 280 g (5.0 mol) of isobutylene. The reaction mixture was heated for one hour at 200° C. The reactor was cooled, vented, and the contents filtered. The filtrate was distilled into four fractions. GLC analysis of the fractions showed that 25.00 g (0.291 mol) of 3-methyl-3-buten-1-ol had been obtained for a yield of 58% based on the starting formaldehyde. The analysis also indicated that 1.0 g of the formate ester of the alkenol had been obtained.

EXAMPLE XVI (Invention)

A one-liter stainless steel autoclave was charged with 200 ml (176 g) of benzene, 16 g of 94.4% paraformaldehyde (0.503 mol), 0.2 g of $\mu,\mu'$-dichlorotetranitrosyldiiron, $[Fe(NO)_2Cl]_2$, and 282 g (5.036 mol) of isobutylene. The reaction mixture was heated at 200° C. for one hour while the pressure (autogeneous) ranged from 1,350 down to 1,050 psig. The reactor was cooled, vented, and the contents filtered. The filtrate was distilled into four fractions. GLC analysis of the fractions indicated that 21.18 g (0.246 mol) of 3-methyl-3-buten-1-ol had been obtained for a yield of 49% based on the starting formaldehyde. The analysis also showed that 0.97 g of the formate ester of the alkenol had been obtained.

EXAMPLE XVII (Invention)

A one-liter autoclave was charged with 200 ml (176 g) of benzene, 16 g of 94.4% paraformaldehyde, 0.5 g of rhodium trichloride, $RhCl_3$, and 291 g (5.196 mol) of isobutylene. The reaction mixture was heated at 200° C. for one hour while the autogeneous pressure ranged from 1,400 down to 1,350 psig. The reactor was cooled, vented, and the contents filtered. The filtrate was distilled into four fractions. GLC analysis of the fractions indicated that 17.53 g (0.204 mol) of 3-methyl-3-buten-1-ol had been obtained for a yield of 40% based on the starting formaldehyde. Analysis showed also that 0.9 g of the formate ester of the above alkenol had been obtained. A small amount of 3-methyl-3-buten-1-ol was also noted in the mixture and was apparently formed by isomerization of the former alkenol.

EXAMPLE XVIII (Invention)

A one-liter autoclave was charged with 200 ml (155 g) of acetonitrile, 16 g of 94.4% paraformaldehyde (0.503 mol), 0.5 g of palladous cyanide, $Pd(CN)_2$, and 292 g (5.214 mol) of isobutylene. The reaction mixture was heated at 200° C. for two hours while the pressure (autogeneous) ranged from 1,750 down to 1,350 psig. The reactor was cooled, vented, and the contents filtered. The filtrate was distilled into four fractions. Analysis of the fractions by GLC indicated that 19.12 g (0.222 mol) of 3-methyl-3-buten-1-ol had been obtained for a yield of 44% based on the starting formaldehyde. Only about 0.1 g of the formate ester of the alkenol was obtained as indicated by the analysis. A considerable amount of unreacted formaldehyde was noted in the reaction mixture, but the quantity was not measured.

EXAMPLE XIX (Invention)

A one-liter stainless steel autoclave was charged with 200 ml (176 g) of benzene, 22 g of 94.4% paraformaldehyde (0.692 mol), 0.5 g of molybdenum dioxide $(MoO_2)$, and 293 g (5.232 mol) of isobutylene. The mixture was heated at 200° C. for one hour while the pressure (autogeneous) ranged from 1,750 down to 1,300 psig. The reactor was cooled, vented, and the contents filtered. The filtrate was distilled into four fractions. GLC analysis of the fractions showed that 33.97 g (0.395 mol) of 3-methyl-3-buten-1-ol had been obtained for a yield of 57% based on the starting formaldehyde. The analysis also showed that 1.45 g of the formate ester of the alkenol was obtained.

EXAMPLE XX (Invention)

A one-liter stainless steel autoclave was charged with 200 ml (176 g) of benzene, 16 g of 94.4% paraformaldehyde, 0.5 g of vanadium (III) acetylacetonate $[V(AcAc)_3]$, and 300 g (5.357 mol) of isobutylene. The mixture was heated at 200° C. for one hour while the pressure (autogeneous) ranged from 1,700 down to 1,600 psig. The reactor was cooled, vented, and the contents filtered. The filtrate was distilled into four fractions. Analysis of the fractions by GLC showed that 21.62 g (0.251 mol) of 3-methyl-3-buten-1-ol had been obtained for a yield of 50% based on the starting formaldehyde. The formate ester was also obtained in the amount of 1.93 g according to the GLC analysis. Considerable unreacted formaldehyde was noted in the reaction mixture, but the amount was not measured.

EXAMPLE XXI (Invention)

A series of three runs was conducted employing vanadyl acetylacetonate [VO(AcAc)₂] as the catalyst for the reaction of formaldehyde with isobutylene. Each of the runs was carried out in the general manner of Example XX employing 200 ml (176 g) of benzene diluent, 16 g of 94.4% paraformaldehyde (0.503 mol), and 0.5 g of VO(AcAc)₂ as catalyst. The results of these runs are shown in Table I below.

TABLE I

| Run No. | Isobutylene, g (mol) | Temp., °C | Time, hr. | Yield Alkenol, %$^{(a)}$ | Formate Ester, g$^{(b)}$ |
|---|---|---|---|---|---|
| 1 | 295 (5.268) | 150 | 1 | 24 | 1.92 |
| 2 | 290 (5.197) | 200 | 1 | 50 | 2.80 |
| 3 | 295 (5.268) | 250 | 0.5 | 34 | 2.49 |

$^{(a)}$3-Methyl-3-buten-1-ol by GLC analysis of distilled product. Yield based on starting formaldehyde.
$^{(b)}$By GLC analysis of distilled product. This material is the formate ester of the alkenol, 3-methyl-3-buten-1-ol.

Example XXII (Invention)

A one-liter stainless steel autoclave was charged with 200 ml (176 g) of benzene, 22 g of 94.4% paraformaldehyde (0.692 mol), 0.5 g of tungstic oxide (WO₃), and 298 g (5.321 mol) of isobutylene. The mixture was heated at 200° C. for one hour while the autogeneous pressure ranged from 2,000 down to 1,300 psig. The reactor was cooled, vented, and the contents filtered. The filtrate was distilled into four fractions. GLC analysis of the fractions showed that 26.35 g (0.304 mol) of 3-methyl-3-buten-1-ol had been obtained for a yield of 44% based on the starting formaldehyde. The analysis also indicated that 0.64 g of the formate ester of the alkenol had been obtained. Considerable unreacted formaldehyde was noted in the reaction mixture, but the quantity was not measured.

EXAMPLE XXIII (Invention)

A series of four runs was carried out which employed a tungsten oxide (WO₃) on silica catalyst for the reaction of formaldehyde with isobutylene according to the instant invention. The composition of the catalyst was as follows: about 8 weight percent WO₃, 0.1 weight percent Al₂O₃, 0.1 weight percent Na₂O, with the balance being silica. Each of the runs was carried out in essentially the same manner as that employed in Example XXII. Each run employed 200 ml (176 g) of benzene diluent, 16 g of 94.4% paraformaldehyde (0.503 mol), and 0.5 g of the finely ground tungsten oxide on silica catalyst described above. The results from these runs are shown below in Table II.

TABLE II

| Run No. | Isobutylene, g (mol) | Temp., °C | Time, hr. | Yield Alkenol, %$^{(a)}$ | Formate Ester, g$^{(b)}$ |
|---|---|---|---|---|---|
| 1 | 245 (4.375) | 125 | 1 | 20 | 0.77 |
| 2 | 325 (5.804) | 175 | 1 | 29 | 0.48 |
| 3 | 293 (5.232) | 200 | 1 | 52 | 0.94 |
| 4 | 280 (5.00) | 275 | 0.33 | 65 | 0.48 |

$^{(a)}$3-Methyl-3-buten-1-ol by GLC analysis of distilled product with yield based on starting formaldehyde.
$^{(b)}$Formate ester of 3-methyl-3-buten-1-ol by GLC analysis of distilled product.

EXAMPLE XXIV (Invention)

A one-liter stainless steel autoclave was charged with 200 ml (176 g) of benzene, 31.5 g of a solution of formaldehyde in methanol which contained 15.09 g (0.503 mol) of formaldehyde, 0.5 g of the finely ground tungsten oxide (WO₃) on silica catalyst employed in Example XXIII, and 305 g (5.446 mol) of isobutylene. The reaction mixture was heated at 200° C. for one hour while the pressure ranged from 1,900 down to 1,500 psig. The reactor was cooled, vented, and the contents filtered. The filtrate was distilled into four fractions. GLC analysis of the fractions showed that 30.41 g (0.354 mol) of 3-methyl-3-buten-1-ol had been obtained for a yield of 70% based on the starting formaldehyde. Only a trace amount of the formate ester of the alkenol was obtained according to the GLC analysis.

EXAMPLE XXV (Invention)

A one-liter stainless steel autoclave was charged with 31.5 g of a solution of formaldehyde in methanol containing 15.09 g (0.503 mol) of formaldehyde, 0.5 g of the finely ground tungsten oxide on silica catalyst employed in Examples XXIII and XXIV, and 290 g (5.179 mol) of isobutylene. The reaction mixture was heated for one hour at 200° C. while the pressure ranged from 1,400 down to 1,300 psig. The reactor was cooled, vented, and the contents filtered with the aid of benzene to rinse out the reactor. The filtrate was distilled into three fractions. GLC analysis of the fractions showed that 24.21 g (0.282 mol) of 3-methyl-3-buten-1-ol had been obtained for a yield of 56% based on the starting formaldehyde. Only a trace amount of the formate ester of the alkenol had been obtained according to the GLC analysis.

In addition to the above-described invention runs and control runs, other control runs were made which employed materials such as tetrabutyl orthotitanate, ammonium nitrate, acid-activated clay (Filtrol 62), and an acidic molecular sieve (SK-500) as catalysts for the reaction of formaldehyde with isobutylene under conditions essentially the same as those employed in Example I in which no catalyst was employed. The yield of 3-methyl-3-buten-1-ol in the above runs was essentially the same as that obtained in said Example I.

Other control runs were carried out using WO₃ on silica or NaHSO₃ as catalysts with aqueous formaldehyde as the reactant rather than the essentially anhydrous formaldehyde used in the runs of this invention. The above-mentioned runs using aqueous formaldehyde gave inferior results in terms of the yield of the desired 3-methyl-3-buten-1-ol and also rather low yields of the product usually obtained when aqueous formaldehyde is reacted with isobutylene according to the Prins reaction, i.e., 4,4-dimethyl-1,3-dioxane.

I claim:
1. A process for the production of alkenols and cycloalkenols which comprises reacting:
 (a) at least one alkene or cycloalkene having at least one allylic hydrogen having the basic structure

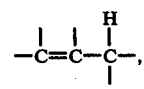

and having from 3 to 20 carbon atoms per molecule with
 (b) formaldehyde in the presence of
 (c) a catalyst selected from the group consisting of organic carboxylic acid salts of Group IB metals under reaction conditions including an elevated temperature and pressure sufficient to produce alkenols and cycloalkenols.

2. A process according to claim 1 wherein (c) can be represented by the general formula $(R-CO_2-)_nM$ wherein R is hydrogen or a hydrocarbyl radical having from 1–19 carbon atoms and wherein $n$ is an integer which is equal to the valence of the metal M in the salt, and wherein M is one of copper, silver, or gold.

3. A process according to claim 1 wherein said reacting is carried out at a temperature in the range of from about 25° C. to about 300° C. and under autogeneous pressure with an amount of catalyst (c) ranging from 0.1 to 10 weight percent based on the weight of formaldehyde present and a molar ratio of (a) to (b) in the range of from 1:1 to 20:1.

4. A process according to claim 1 wherein said reacting is carried out in an inert reaction diluent.

5. A process according to claim 1 for the production of 3-methyl-3-buten-1-ol which comprises reacting (a) isobutylene with (b) formaldehyde at a temperature in the range of from about 150° C. to about 250° C. under autogeneous pressure.

6. A process according to claim 5 wherein said catalyst is silver acetate or cupric acetate monohydrate.

7. A process according to claim 1 wherein (a) is isobutylene and said reacting is carried out in benzene as a reaction diluent and in the presence of (c) silver acetate or cupric acetate monohydrate.

* * * * *